United States Patent [19]

Pompa

[11] Patent Number: 5,320,529
[45] Date of Patent: Jun. 14, 1994

[54] METHOD AND APPARATUS FOR LOCATING AN IDEAL SITE FOR A DENTAL IMPLANT AND FOR THE PRECISE SURGICAL PLACEMENT OF THAT IMPLANT

[75] Inventor: Daniel G. Pompa, Roslyn Heights, N.Y.

[73] Assignee: Howard C. Weitzman, Woodmere, N.Y. ; a part interest

[21] Appl. No.: 942,752

[22] Filed: Sep. 9, 1992

[51] Int. Cl.⁵ .............................................. A61C 3/02
[52] U.S. Cl. .................................... 433/76; 433/214; 433/215; 434/270; 434/263
[58] Field of Search .................. 433/75, 76, 213, 214, 433/215, 173; 434/263, 270

[56] References Cited

U.S. PATENT DOCUMENTS

| | | |
|---|---|---|
| 4,741,698 | 5/1988 | Andrews . |
| 4,767,328 | 8/1988 | Branemark . |
| 4,784,608 | 11/1988 | Mays . |
| 4,815,974 | 3/1989 | Scortecci . |
| 4,872,840 | 10/1989 | Bori . |
| 4,875,857 | 10/1989 | Kubein-Messenberg et al. ... 433/75 |
| 4,884,970 | 12/1989 | Mays . |
| 4,906,191 | 3/1990 | Soderberg . |
| 4,931,016 | 6/1990 | Sillard . |
| 4,960,381 | 10/1990 | Niznick . |
| 4,998,881 | 3/1991 | Lauks .................... 433/76 |
| 5,015,183 | 5/1991 | Fenick . |
| 5,057,017 | 10/1991 | Sillard ................... 433/173 |
| 5,133,660 | 7/1992 | Fenick ................... 433/76 |

OTHER PUBLICATIONS

Jeffcoat, et al., "Planning Interactive Implant Treatment with 3-D Computed Tomography," *JADA*, vol. 122, Nov. 1991, p. 40.

Karellos et al., "Transfer of CT Scan Data to Diagnostic Casts," *Implant Dentistry*, vol. 2, No. 2 (1993), p. 97.

Saadoun, et al., "Implant Positioning for Periodontal, Functional and Aesthetic Results," *International Chronicle*, vol. 4, No. 7, p. 43.

Zinner, Small and Francis, "Presurgical Prosthetics and Surgical Templates," Dental Clinics of North America, vol. 33, No. 4, Oct. 1989.

Misch and Crawford, "Predictable Mandibular Nerve Location–A Clinical Zone of Safety", *Denistry Today*, p. 30. Dec. 1990.

Stoker, Mankovich, and Valentino, "Stereolithographic Models for Surgical Planning," J. Oral Maxillofc. Surg., 50:466–470, 1992.

*Primary Examiner*—Gene Mancene
*Assistant Examiner*—Todd E. Manahan
*Attorney, Agent, or Firm*—Collard & Roe

[57] ABSTRACT

An apparatus and method for locating and surgically positioning a hole for an implant and holder in a jawbone of a patient includes constructing a model of a jawbone. A structure is located within the model depicting variations in density within the jawbone. A hole is drilled into the model based on the location of the structure. A rod is placed into the hole and a guide template is fabricated around the model which forms a bore around the rod. The guide template is placed onto the jawbone of the patient and a hole is drilled through the bore into the jawbone to make a hole in the jawbone along the same path as the hole in the model for receiving the implant and holder.

17 Claims, 3 Drawing Sheets

METHOD AND APPARATUS FOR LOCATING AN IDEAL SITE FOR A DENTAL IMPLANT AND FOR THE PRECISE SURGICAL PLACEMENT OF THAT IMPLANT

BACKGROUND OF THE INVENTION

1. Field of the Invention

The present invention relates to a method and apparatus for locating a site and surgically positioning a dental implant. More specifically, it relates to a method and apparatus for placing an endosseous dental implant into the most optimal bone structure of a patient's upper or lower jawbone utilizing a surgical guide template that is fabricated with the use of computerized tomography and stereolithography.

2. The Prior Art

In the field of dentistry, tooth implants are increasingly being utilized. In the articles "Predictable Mandibular Nerve Location—A Clinical Zone of Safety" by Misch and Crawford, appearing in Dentistry Today, December, 1990, p. 32, and "Presurgical Prosthetics and Surgical Templates" by Zinner, Small and Panno, appearing in Dental Clinics of North America (Vol. 33, No. 4, October, 1989); and the U.S. Pat. No. 5,015,183 to Fenick describe the present state of the art regarding the placement of oral implants with a surgical template and the inherent restrictions and limitations thereof. A problem in the art and science of placing dental implants is finding and locating sufficient bone structure in height, length and width in which to fix the implant so as to obtain the most optimum long term success. In general, the longest length implant that can be placed into the greatest dimensions of bone will give the best long term prognosis.

An inherent problem exists with placing an implant into the human lower jaw. The alveolar nerve (Cranial Nerve V, Division III) passes through a canal entering the posterior areas of a human jaw and coursing through it. As a result, a surgeon is limited by the depth to which he can place an implant and presently will stay safely above the nerve, as discussed in detail in the article "Predictable Mandibular Nerve Location—A Clinical Zone of Safety." This zone of safety restricts the surgeon to only utilizing approximately one-third to one-half of the full height of available bone depending on individual anatomical variation. If an implant impinged upon the nerve, the patient could lose feeling in their lower lip and chin on the affected side. Since the location of the nerve is difficult to pinpoint during the surgical procedure with present technology, the longer more desirable types of endosseous implants generally are not used in the area of the posterior lower jaw.

If an implant could be placed in the lower posterior jaw and engage the lower portion (inferior border) this would result in improved long term prognosis. The resulting implant could be twice the length achieved by present technology.

Presently, to place an implant into the inferior border of the posterior mandible (lower jaw) it is necessary to perform a nerve transposition procedure. This involves the dissection of the nerve from its canal, followed by placing the implants. Then the nerve is repositioned around the implants. The morbidity associated with this procedure is significant. (Howard Davis, D.D.S., 1992 August, American Association of Periodontics, Chicago, Illinois—Clinical Meeting.)

Alternatively, the surgeon could use the information on a standard C.T. scan and approximate the angle of the site for the implant. However, this method presents a risk of damage to the inferior alveolar nerve which can result in altered or no sensation to the lip and chin on the affected side. The worse case scenario is an irreversible loss of feeling to the lower lip, chin and gum tissue on that side. There is a large margin for error with this method due to a lack of precision in achieving the correct angle to direct the bur during the surgical procedure of placing the implant.

Also known from the prior art are stereolithographic models (SLA Models) constructed from digital image data (computerized tomography) which allows the surgeon to view the external and internal anatomy prior to surgery, as described in the article entitled "Stereolithographic Models for Surgical Planning: Preliminary Report" by Stoker, Mankovich and Valentino, J. of Oral and Maxillofacial Surgery, May 1992, p,. 466–471. However, stereolithographic models have not been used to place dental endosseous dental implants into the most optimal jawbone location and have not been used to specifically avoid contacting the inferior alveolar nerve and more specifically to actually bypass this structure thereby engaging the lowermost portion of the jaw.

This SLA Model also gives the operating surgeon the precise information (optimal height, length and depth of bone) that is needed to fabricate a specially designed surgical template to be used in any area of the upper or lower jaw.

SUMMARY OF THE INVENTION

It is therefore an object of the present invention to provide a method and apparatus for locating a site and surgically positioning a dental implant which overcomes the drawbacks of the prior art and allows more accurate and precise placement of dental implants.

It is a further object of the present invention to reduce the risk of morbidity following the placement of an implant.

It is still a further object of the present invention to select the most ideal location with respect to the length and diameter for a dental implant.

It is still a further object of the present invention to provide a path for the implant which avoids the inferior alveolar nerve in the lower jaw.

It is still another object of the present invention to provide a method and apparatus for drilling a bore along a predetermined trajectory into the most optimal bone structure of an upper or lower jaw.

These and other related objects are achieved according to the present invention by a method and apparatus for locating and surgically positioning a hole for an implant and holder in a jawbone of a patient to avoid a vital structure or structures, i.e., a sensory nerve (Cranial Nerve V, Division III), or engage a bone structure.

The apparatus according to the invention for directing a bur includes a jawbone model formed by a method of scanning the jawbone with computerized tomography and constructing a stereolithographic model including a radiopaque (marker) representing the inferior alveolar nerve. The apparatus also includes a means for locating and drilling a hole in the model to avoid the radiopaque marker and a simulated implant (implant analog) is placed into the hole. A holder is then placed into this implant analog and protrudes above this implant analog. Then a guide template is fabricated on the jawbone model including a bore formed around the holder so that when the template is now transferred and placed on the jawbone of the patient, a specifically designed drill is guided by the template bore into the jawbone along the same path as the hole in the model to avoid the nerve and forms a hole for receiving the actual implant and holder. Alternatively, the apparatus also includes a means for locating and drilling a hole in said model to precisely engage a specific bony structure.

The apparatus also includes a surgical guide ring having a cylindrical body with two ends. An outwardly extending flange is located at one end of the surgical guide ring with an aperture extending along the central axis of the cylindrical body from one end to the other end. The surgical guide ring is placed within the bore of the guide template to further guide the drill, giving a higher degree of accuracy and less margin for error. The surgical guide ring is to be used with the SLA generated surgical guide template to allow an implant to engage optimal bone structure in any location of the upper (maxillary) or lower (mandibular) jaw.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several

DETAILED DESCRIPTION OF THE PREFERRED EMBODIMENT

Figure 1A:
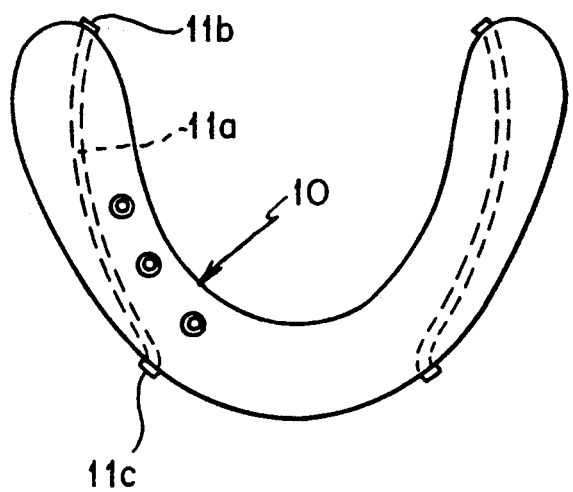
FIG. 1a is a top plan view of a model of a jawbone.
Figure 1B:
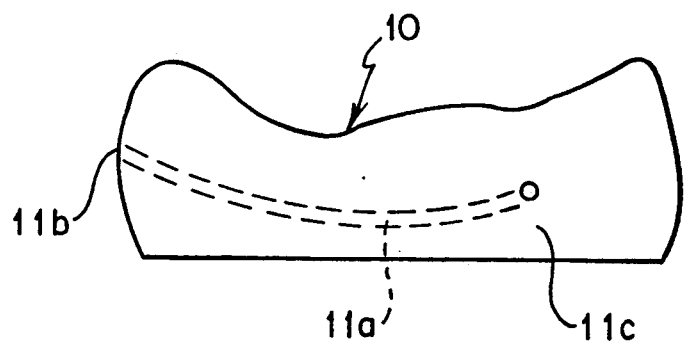
FIG. 1b is a left side elevational view of the model.

Referring now to the drawings and, in particular, FIGS. 1a and 1b, there is shown a stereolithographic (SLA) model 10 of a human jawbone. A computed tomography (CT) scan is performed on the individual requiring a dental implant. The information from the scan can then be processed to generate a clear acrylic model 10 showing both interior structures and exterior contours. The stereolithographic process is discussed in detail in the article, "Stereolithographic Models for Surgical Planning: Preliminary Report" by Stoker, Mankovich and Valentino which appears in the Journal of Oral and Maxillofacial Surgery, 50:466–471, 1992, the subject matter which is incorporated by reference into this patent.

Since the stereolithographic model displays both outer contours and inner anatomic structures, a nerve canal 11a is shown corresponding to the inferior alveolar nerve which is a radiolucent canal. The canal enters the jaw on the inner aspect 11b (medial) and exits the lower jaw on the outer aspect 11c (lateral) at the mental foramen. A radiopaque marker 11d is placed into canal 11a, so that the location of the nerve can be easily seen and X-rayed. Radiopaque marker 11d can be fabricated from a twisted pair of 26 gauge stainless steel wire or a pipe cleaner, for example. Other structures are present in model 10 corresponding to radiopaque bony areas of the jawbone.

Figure 2A:
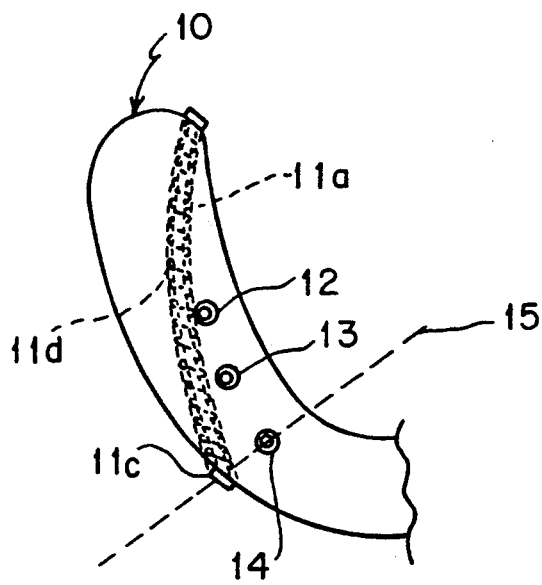
FIG. 2a is a top plan view of the model showing proposed implant sites.

As can be seen in FIG. 2a, when looking from the top of model 10, a surgeon can easily locate radiopaque marker 11d and sites 12, 13 and 14 can be drilled into model 10 avoiding 11d. This is a technique known as "model surgery" where surgery is performed on a model of the patient prior to the actual surgery being performed. Oral and Maxillofacial surgeons routinely perform this procedure with other surgical endeavors, i.e., orthognathic surgery. With the transparent model, radiopaque marker 11d is easily visible and thus avoidable. With the present information, the actual operating surgeon will perform the model surgery and educational "hands on" programs will be offered. The SLA generated model also reveals to the surgeon where deformities exist so that the surgeon can carefully plan what areas may be augmented (grafted) prior to surgery, as a separate procedure or at the same time the implants are placed.

Model surgery is then performed on the SLA model with the marker in place. Site 14, the most anterior site is placed just medial (lingual) of the mental foramen. It is also placed in a vertical plane 15 which passes through the mental foramen and is generally perpendicular to the surface of the model above and/or below the mental foramen. Since the nerve 11a exits laterally at outer aspect 11c, site 14 is in a relatively safe position. Sites 13 and 12 are placed toward the posterior mandible. When placing the bur channel, the surgeon can visualize radiopaque marker 11d within model 10 in three dimensions. After drilling, the sites are fitted with the implant analogs 22, 23 and 24. Implant analogs 22, 23 and 24 fit entirely within sites 12, 13 and 14. It should be noted that implant analogs 22, 23 and 24 are radiopaque.

Figure 2B:
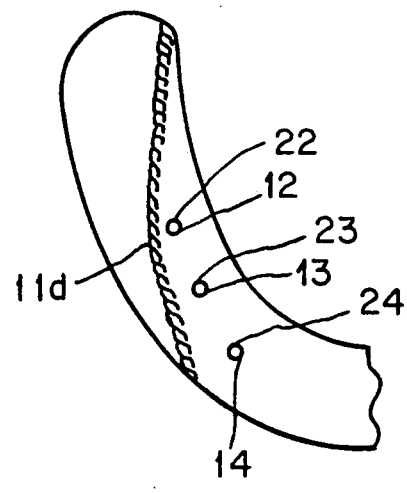
FIG. 2b is a top plan view of an x-ray of the model from FIG. 2a with an opaque marker and implant analogs in place.

An X-ray, as shown in FIG. 2b, from above (occlusal view) is then taken of model 10 to determine whether an appropriate safety margin is established between radiopaque marker 11d and implant analogs 22, 23 and 24. If any of the implant sites encroach marker 11d, then that site will be adjusted away from marker 11d. A surgical zone of safety of 2 mm is established as described in the article "Predictable Mandibular Nerve Location—A Clinical Zone of Safety" by Misch and Crawford. Sites 12, 13 and 14 can be alternately moved until all sites are at least 2 mm away from opaque marker 11d and confirmed by X-ray analysis.

Figure 3:
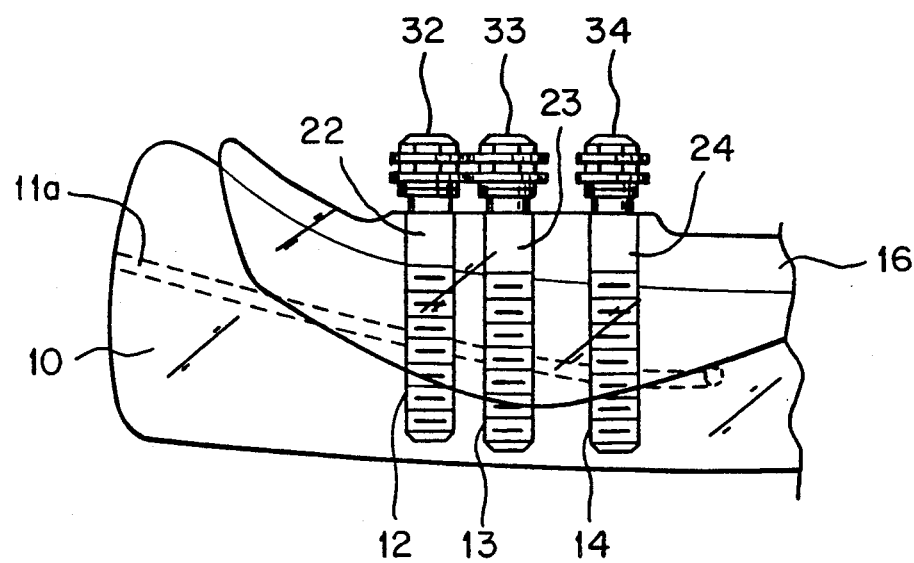
FIG. 3 is a side-elevational view of the model with implants, holders and template.

As can be seen in FIG. 3, implant analogs 22, 23 and 24 bypass radiopaque marker 11d which represents nerve 11a, which was previously a boundary limiting structure. Holders 32, 33 and 34 are then attached to implant analogs 22, 23 and 24. Holders 32, 33 and 34 extend upwardly from implant analogs 22, 23 and 24 outside of sites 12, 13 and 14. A surgical guide template 16 is made, for example, from clear acrylic by placing it around model 10 and holders 32, 33 and 34. Surgical guide template 16 is made, for example, by Nealon's Technique (resin restoration) available from Fricke International, Illinois, or any other powder and liquid technique from model 10, and incorporates one or more guide paths for the bur. The guide path is formed by holders 32 33 and 34 which extend along the longitudinal axis of implant analogs 22, 23 and 24 which are in sites 12, 13 and 14 through template 16. Guide template 16 is approximately 5 mm thick and can be used to aid in preventing the bur from developing its own path during actual surgery. The thickness of guide template 16 is determined by the exposed portion of holders 32, 33 and 34, i.e., the portion extending above model 10.

Figure 4A:
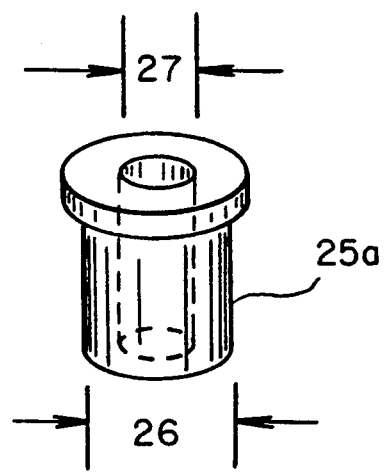
FIG. 4a is an enlarged perspective view of a surgical guide ring.
Figure 4B:
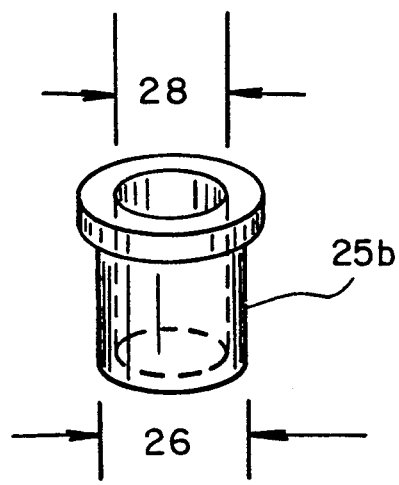
FIG. 4b is an enlarged perspective view of an alternate embodiment of a surgical guide ring.

As can be seen in FIGS. 4a and 4b, the surgical guide rings 25a and 25b are additionally provided to improve the accuracy of the guide path of template 16. Guide rings 25a and 25b are made of hard material, which is resistant to chipping. The material can be fabricated from, for example, a titanium alloy, a chrome-cobalt alloy, or a titanium-chrome-cobalt alloy. Ideally, the material is titanium 6,4 (90% titanium, 6% aluminum, and 4% vanadium). Surgical guide rings 25a and 25b are provided with different internal diameters 27 and 28, but similar external diameters 26 which match that of the external dimension of holders 32, 33 and 34 and will therefore fit exactly in the hole (bore) created by these holders within surgical guide template 16.

Surgery is then performed on the patient. All this information including precise predetermined angulations can then be transferred to a surgical guide template, which is placed on the patient's upper or lower jawbone.

Figure 5:
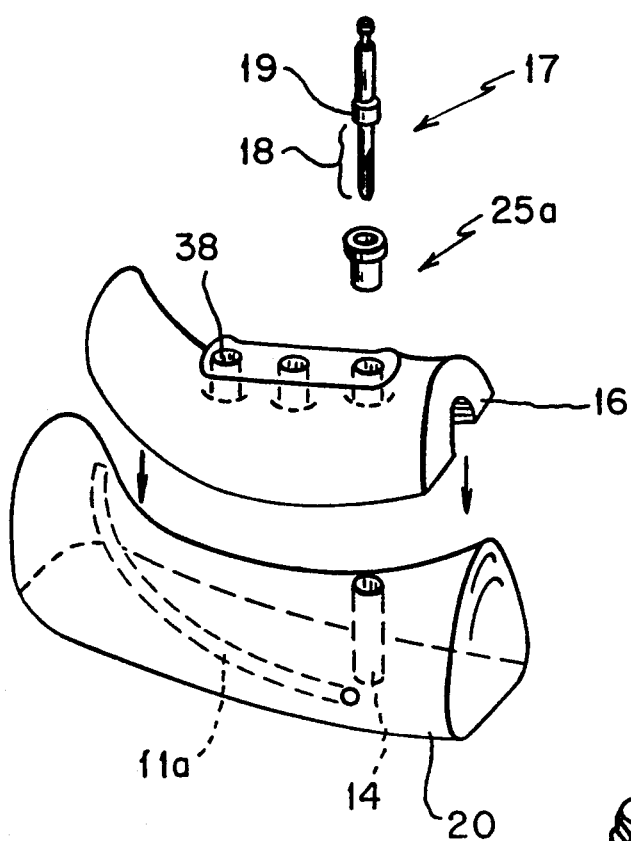
FIG. 5 is an exploded view of a jawbone, template, guide rings and bur.

FIG. 5 shows the completed guide template 16 which is now placed on the patient's lower jawbone 20, not model 10. Surgical guide ring 25a is placed into a bore 38 of template 16 to provide a guide for drill or bur 17 as it penetrates jaw 20. Bur 17 will follow the path of site 14 which was made during model surgery when the surgeon visualized the location of opaque marker 11d which represented nerve 11a, i.e., in a vertical plane which passes through the mental foramen and is generally perpendicular to the surface of the model above and/or below the mental foramen.

The first hole to be drilled is at site 14' having the greatest distance from nerve 11a, i.e., that site with the largest safety margin. Initially, guide ring 25a having a smaller inner diameter is used along with a smaller bur to drill a pilot hole. Then surgical guide ring 25b, and a corresponding larger bur, can enlarge the hole. A series of surgical guide rings and burs may be used to enlarge the hole to a desired size. Since the surgical guide rings have the same external diameters, they can easily be substituted into the bores of guide template 16. Burs 17 are provided with markings along a lower cutting region 18 to indicate depth as the bur cuts into jawbone 20. (These markings are height adjusted to accommodate the depth of guide template 16 and guide ring 25a.) The surgeon can then read the depth right off of bur 17 without having to subtract the depth of template 16 and guide ring 25a. Above lower cutting region 18 is a stop 19 which limits the depth to which bur 17 can be inserted into jawbone 20.

Figure 6:
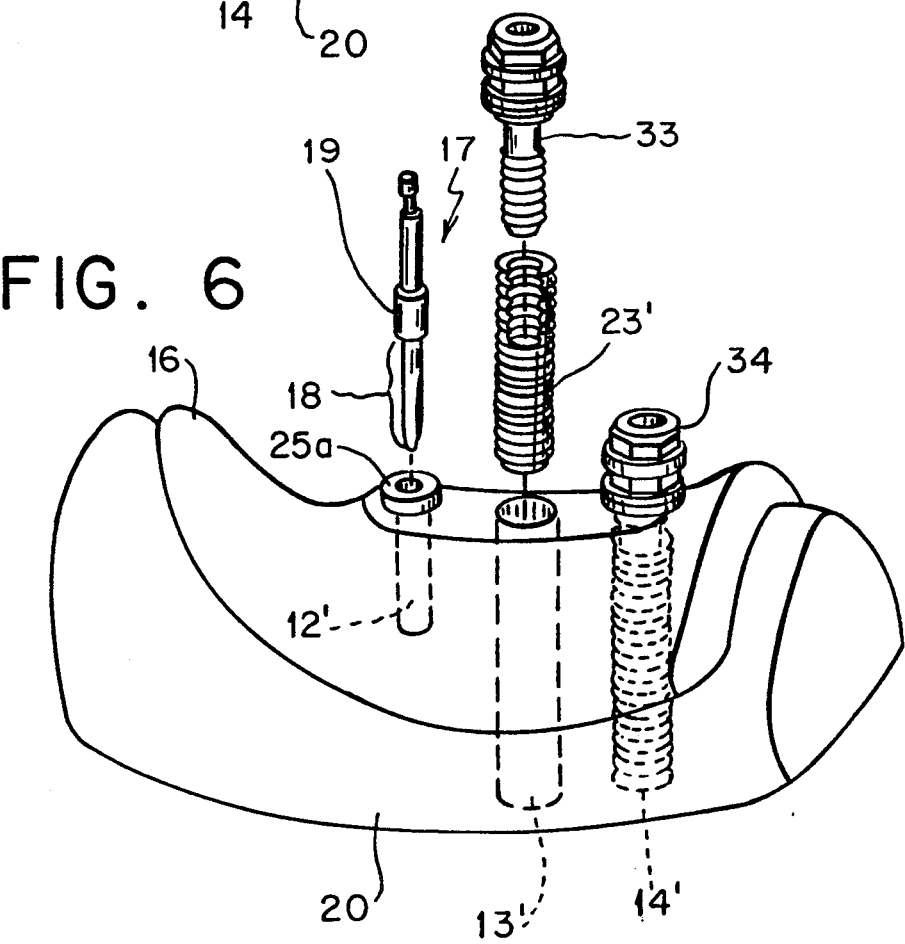
FIG. 6 is a perspective view showing the template with guide rings held in place by a holder.

As can be seen in FIG. 6, the first implant 24' is placed into the patient at site 14', followed by surgical holder 34 which is placed through template 16 and tightened to implant 24' to secure template 16 to jaw 20. This locks template 16 into place and increases the accuracy when subsequent holes, e.g., sites 13' and 12', are drilled corresponding to site 13 and site 12. The implants are provided with threads along their exterior and interior. The external threads may be self-tapping into jawbone 20 or a separate tap may be used prior to inserting the implant, based upon the jawbone density. Once implant 24' is inserted, the exterior threads of holder 34 is screwed into the internal threads of implant 24'. Other holes are created, i.e., into sites 13', 12' with the use of guide rings and specialized burs and the implants are placed. The holders are removed from the implants and a cover screw is placed into each implant and the area is irrigated and closed. It should be noted that the implants, for example, titanium or titanium-alloy implants have a high degree of bone biocompatibility.

The implants, which are placed according to the invented described method, bypass the inferior alveolar canal and engage the inferior border of the mandible.

It should be noted that any surgical procedure requiring precise knowledge of optimal bone dimensional anatomy and any procedure performed in bone in the vicinity of a vital structure, i.e., nerve, artery, vein, etc., can benefit from the method and apparatus disclosed herein. In areas of the human upper (maxillary) and lower (mandible) jaw, other than the posterior lower (mandible) jaw, this method and apparatus can also be of a great advantage to the patient and surgeon. For example, in the maxillary jaw, there are a number of dense areas of bone (the ptergoid plate convergence posterior to the maxillary tuberosity and the junction of the lateral nasal wall and medial antral wall) which in a severely resorbed upper (maxillary) jaw are the most ideal sites to engage. Up to the present time, the degree of accuracy and precision available to place implants into these areas is limited at best. With the STA Generated Model, a replica of the maxillary sinus wall, nasal wall and ptergoid plates will be precisely replicated and as described in this invention, the operating surgeon can perform model surgery on a clear model and transfer that information to the guide template and follow the same method as described for precise and accurate placement into these sites. The ability to perform precise placement can actually result in a less significant surgical procedure. Many of these patients with a resorbed maxillary upper jaw would need a pre-implant surgery to graft or augment the area and then have a second procedure performed to place the implants. The graft and augmentation procedure may be avoided with the ability to place implants with the precision described herein.

While only a single embodiment of the present invention has been shown and described, it is to be understood that many changes and modifications may be made thereunto without departing from the spirit and scope of the invention as defined in the appended claims.

What is claimed is:

1. A method for locating and surgically positioning a hole for an implant and holder in a jawbone of a patient comprising the steps of:
   i.) constructing model of the jawbone including inner anatomic structures;
   ii.) locating a structure within the model depicting variations in density within the jawbone;
   iii.) drilling a hole into the model based on the location of the structure;
   iv.) placing a rod into the hole;

v.) fabricating a guide template around the model and forming a bore around the rod; and vi.) placing the guide template onto the jawbone of the patient and drilling through the bore into the jawbone to make a hole in the jawbone along the same path as the hole in the model for receiving the implant and holder.

2. The method according to Claim 1, wherein the rod includes a simulated implant analog and a holder.

3. The method according to Claim 2, wherein said step of constructing a model of the jawbone comprises:

scanning the jawbone with a computerized tomography scan to create a computer image;

tracing anatomical structures within the image; and constructing a stereolithographic model of the jawbone based on the anatomical structures and information reformatted from the computerized tomography scan.

4. The method according to Claim 3, wherein said step of locating a structure includes locating a structure within the model depicting a radiopaque bony area within the jawbone; and said step of drilling a hole includes drilling a hole in the model to penetrate and engage the structure.

5. The method according to Claim 3, wherein said step of locating a structure includes locating a structure within the model depicting a radiolucent canal within the jawbone, and said step of drilling a hole includes drilling a hole into the model to avoid the structure.

6. The method according to Claim 5, wherein said step of drilling a hole into the model and avoiding or engaging the structure includes verifying the position of the hole by radiographic analysis.

7. The method according to Claim 6, additionally including the step of:

placing a surgical guide ring into the bore of the template, prior to the step of placing the template onto the jawbone of the patient.

8. The method according to Claim 7, additionally including the step of selecting a surgical guide ring having an internal diameter which is precisely machined to be slightly larger than the external diameter of a drill, so that the drill is accurately guided into the jawbone along the same path as the hole in the model that is created during model surgery prior to the step of placing a surgical guide ring into the guide template.

9. An apparatus for locating and surgically positioning a hole for an implant and holder in a jawbone of a patient comprising:

a jawbone model including inner anatomic structures formed by a method of scanning the jawbone with computed tomography and constructing a stereolithographic model including a structure within said model depicting variations in density within the jawbone;

means for locating and drilling a hole in said model based on the location of said structure;

a rod placed into the hole; and a guide template disposed on said jawbone model including a bore formed around said rod so that when said template is placed on the jawbone of the patient, a drill is guided by said template bore into the jawbone along the same path as the hole in said model to form a hole for receiving the implant and holder.

10. The apparatus according to Claim 9, wherein said jawbone model is constructed from digital image data of the jawbone.

11. The apparatus according to claim 10, wherein said structure within said model depicts a nerve canal with the hole being drilled at least 2 mm away from said structure.

12. The apparatus according to claim 11, wherein said structure within said model depicts a dense bony area with the hole being drilled to engage said structure.

13. The apparatus according to Claim 11, wherein said jawbone model is created from a translucent material.

14. The apparatus according to Claim 11, additionally including a surgical guide ring having a cylindrical body with two ends, and an outwardly extending flange at one end thereof and an aperture located along a central axis of said cylindrical body extending from one end to the other end, wherein said surgical guide ring is placed within the bore of said guide template to further guide the drill.

15. The apparatus according to Claim 14, wherein said surgical guide ring is made of a hard material which resists chipping.

16. The apparatus according to Claim 15, wherein the material is selected from a group consisting of a titanium alloy, a titanium-cobalt alloy, or a titanium-chrome-cobalt alloy.

17. The apparatus according to Claim 16, additionally including a series of surgical guide rings having the same external diameter and varying internal diameters, each corresponding to a particular drill, the internal diameter of each guide ring is slightly larger than an external diameter of the corresponding drill.

* * * * *